United States Patent [19]
Itani et al.

[11] Patent Number: 5,776,414
[45] Date of Patent: Jul. 7, 1998

[54] PHYSIOLOGICAL TISSUE TREATMENT APPARATUS

[75] Inventors: Kazunori Itani; Kouhei Kihara; Shogo Iijima, all of Mitaka, Japan

[73] Assignee: Aloka Co., Ltd., Tokyo, Japan

[21] Appl. No.: 788,547

[22] Filed: Jan. 24, 1997

[51] Int. Cl.$^6$ .................................................. G01N 35/10
[52] U.S. Cl. .................................... 422/67; 422/58; 422/63; 422/65; 422/102; 436/43; 436/46; 436/48; 436/50
[58] Field of Search .......................... 422/63, 99, 100, 422/102, 67, 104, 58; 436/43, 46, 48, 49, 50, 54, 174, 180

[56] References Cited

U.S. PATENT DOCUMENTS

| | | | |
|---|---|---|---|
| 4,738,824 | 4/1988 | Takeuchi | 422/63 |
| 4,908,319 | 3/1990 | Smyczek et al. | 435/285 |
| 4,909,992 | 3/1990 | Bjorkman | 422/100 |
| 5,068,091 | 11/1991 | Toya | 422/99 |
| 5,273,905 | 12/1993 | Muller et al. | 435/301 |
| 5,424,040 | 6/1995 | Bjornsson | 422/101 |
| 5,573,727 | 11/1996 | Keefe | 422/63 |
| 5,589,137 | 12/1996 | Markin et al. | 422/104 |
| 5,686,313 | 11/1997 | Sitte et al. | 436/176 |

*Primary Examiner*—Long V. Le
*Attorney, Agent, or Firm*—Fishman, Dionne, Cantor & Colburn

[57] ABSTRACT

A physiological tissue sample on a glass slide is treated by a reagent. A reagent bath is formed so that its horizontal depth becomes progressively larger from the lower part to the upper part. In a first treatment mode, a small amount of reagent is introduced in the reagent bath, and a sample plate is introduced into the bath up to a first treatment position. In a second treatment mode, a large amount of reagent is introduced in the reagent bath, and a sample plate is introduced into the bath up to a second treatment position.

13 Claims, 3 Drawing Sheets

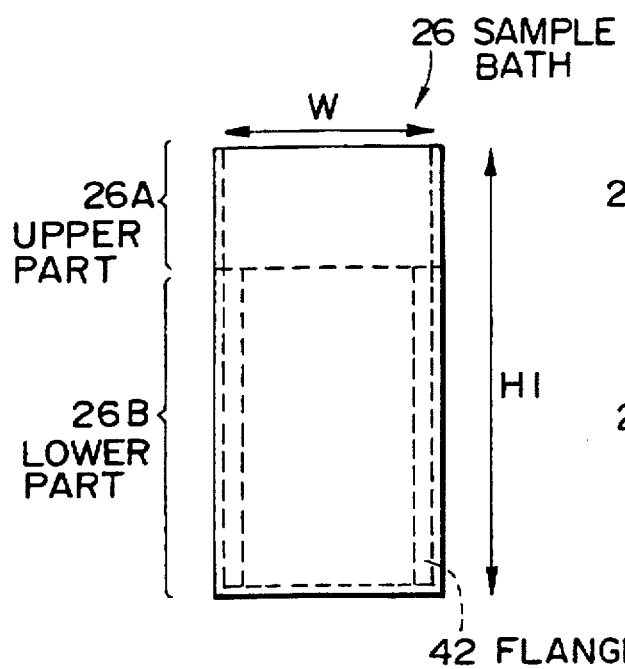
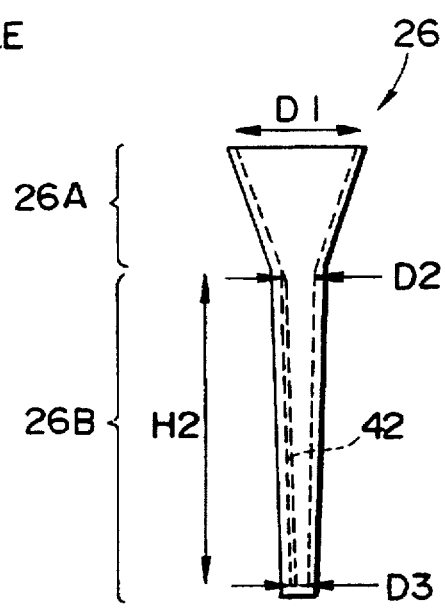
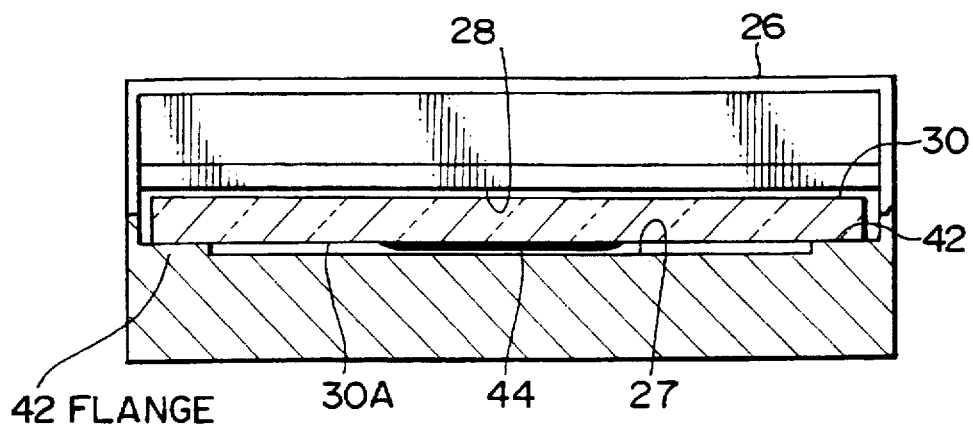

LARGE REAGENT AMOUNT

SMALL REAGENT AMOUNT

5,776,414

PHYSIOLOGICAL TISSUE TREATMENT APPARATUS

BACKGROUND OF THE INVENTION

1. Field of the Invention

This invention relates to an apparatus for processing physiological tissue samples with reagents.

2. Description of the Prior Art

Recently, due to advances made in the field of biotechnology, a great deal of study on physiological tissue is being carried out in research institutes and universities. In these procedures, a physiological tissue sample is treated by one or more reagents. For example in the case of immunological staining and ISH (in situ hybridization), a thin section of physiological tissue (referred to hereafter as sample) is mounted on a transparent sample plate (referred to hereafter as glass slide), and various procedures such as dehydration, staining and hybridization are performed on the sample on the slide.

In this kind of processing, a plurality (e.g. 20) of glass slides on which samples had been mounted were disposed in a metal cage, these slides being separated by a fixed interval. This cage was then immersed in a large glass reagent bath, and treatment was performed using the cage and reagent bath for each reagent.

However according to this conventional treatment method, introduction of reagents into the bath and reagent removal after treatment was work using the hands, and therefore troublesome. Further, as a large reagent bath had to be used to immerse a large number of glass slides all at once, a large amount of reagent was always required.

Although some procedures such as removal of paraffin for example require a large amount of reagent, there are also many procedures which can be satisfactorily accomplished with only a small amount of reagent. In particular, when a costly reagent is used, it is advantageous from a cost viewpoint to perform the procedure with the minimum possible amount of reagent. In the prior art, as it was always necessary to use a large amount of reagent regardless of the reagent type, it was impossible to achieve cost reductions.

Moreover, in the prior art, disposal of reagent after use, i.e. reagent discharge, also posed a problem.

SUMMARY OF THE INVENTION

In view of the above problems, it is therefore an object of this invention to provide a physiological treatment apparatus that prevents waste of reagent.

It is a further object of this invention to provide a physiological treatment apparatus which can be used for treatment by a large amount of reagent, and treatment by a small amount of reagent.

It is yet a further object of this invention to provide a compact apparatus at a lower cost.

In order to achieve the above objects, an apparatus for treating a physiological tissue sample on a sample plate by a reagent comprises:

a reagent bath for inserting sample plates, the cross-sectional surface area of the upper part of the bath being larger than that of the lower part of the bath, and control means for controlling transport of sample plates and supply of reagents, wherein:

in a first treatment mode, a first amount of reagent is supplied to the bath, and the sample plate is inserted in the bath up to a first treatment position, and in a second treatment mode, a second amount of reagent is supplied to the bath, and the sample plate is inserted in the bath up to a second treatment position, this second amount being larger than this first amount, and this second treatment position being higher than this first treatment position.

According to the above construction, the second treatment mode is selected when it is desired to perform treatment using a large amount of reagent, and the first treatment mode is selected when it is desired to perform treatment using a small amount of reagent.

In the first treatment mode and the second treatment mode, the amount of reagent is different, and the depth to which the plate is inserted is also different. The sample plate is positional at a higher level in the reagent bath in the second mode than in the first mode.

According to this invention, the same reagent bath may be used for the first treatment mode and the second treatment mode, so apparatus costs can be reduced. Moreover the amount of reagent used can be reduced, so treatment costs can be reduced.

An embodiment of this invention comprises means for selecting the first treatment mode or the second treatment mode according to the type of reagent used.

In the embodiment of this invention, the horizontal depth of the reagent bath progressively increases from the lower part to the upper part.

An embodiment of this invention comprises plate positioning means for preventing the sample on the sample plate from coming in contact with the inner wall of the reagent bath. Herein, this plate positioning means is preferably at least one flange formed on the inner wall of the reagent bath.

An embodiment of this invention, the control means periodically raises and lowers the reagent plate while treatment by a reagent is being performed. The reagent is therefore stirred which increases the efficiency of treatment.

BRIEF DESCRIPTION OF THE DRAWINGS

FIG. 2 is a front view of a reagent bath according to this invention.

FIG. 3 is a lateral view of a reagent bath according to this invention.

FIG. 4 is a partial view in horizontal section showing a glass slide inserted in a reagent bath.

DESCRIPTION OF THE PREFERRED EMBODIMENTS

Figure 1:
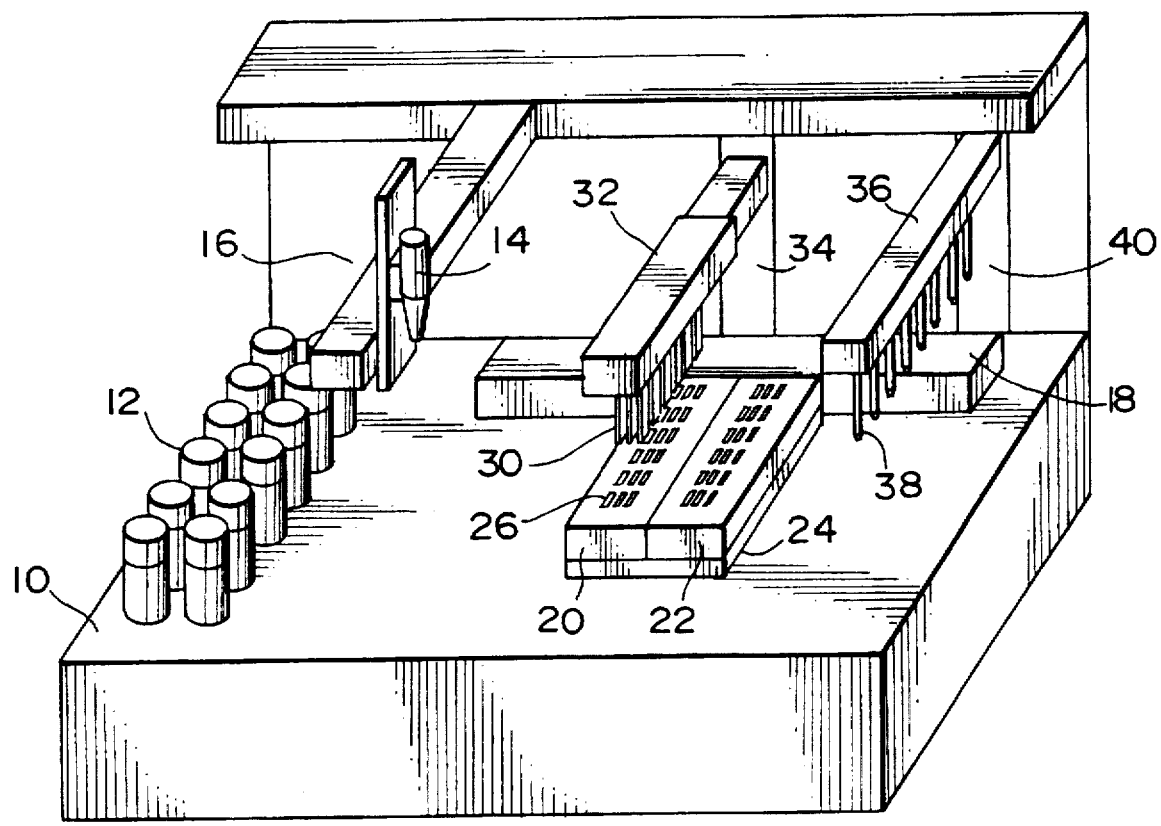
FIG. 1 is a perspective view of a physiological tissue treatment apparatus according to this invention.

FIG. 1 is a perspective view of a physiological tissue treatment apparatus according to this invention.

In FIG. 1, a plurality of reagent containers 12 are disposed on the body 10 of an apparatus. A pipette nozzle 14 aspirates reagent from one of the reagent containers 12, and discharges the reagent to a reagent bath 26 described hereafter. The pipette nozzle 14 is transported by a transport mechanism 16. The pipette nozzle 14 can move freely in three dimensions. A horizontal stage 18 is provided on the body 10 of the apparatus. Two treatment units 20, 22 are driven in a horizontal direction by this horizontal stage 18. A temperature controller 24 comprising a heating plate or the like is disposed underneath the treatment units 20, 22. The assembly comprising the two treatment units 20, 22 and temperature controller 24 is driven in a horizontal direction by the horizontal stage 18.

The treatment units 20, 22 have an identical construction. A plurality of reagent baths 26 are formed in the treatment units 20, 22. The reagent baths 26 will be described in detail hereafter.

A holding mechanism 32 holds a plurality of glass slides 30. The holding mechanism 32 is driven in an up/down direction by an up/down stage 34. The mechanism 32 holds a plurality of rows (e.g. 3 rows) of the glass slides 30. A plurality of the reagent baths 26 are arranged in rows corresponding to the rows of glass slides. The reagent baths 26 are separate from one another. Different reagents can therefore be introduced into the reagent baths so as to simultaneously perform different treatments on each of the glass slides 30.

A plurality of fine-tipped aspirating nozzles 38 are provided in an aspirating unit 36. These aspirating nozzles 38 are used to aspirate and remove reagent remaining in the baths 26 after reagent treatment. The aspirating unit 36 is driven in an up/down direction by an up/down stage 40. The aspirating nozzles 38 are arranged in rows with an identical pitch to that of the rows of reagent baths 26.

FIG. 2 and FIG. 3 show the construction of one of the reagent baths 26. FIG. 2 shows the construction of the bath 26 viewed from the front, and FIG. 3 shows the construction of the bath viewed from the side.

The reagent bath 26 is a container (or well) into which a reagent can be introduced. As shown in FIG. 3, the horizontal depth of the bath progressively increases from bottom to top. In other words, the cross-sectional surface area of the bath 26 in a horizontal direction progressively increases from bottom to top.

Describing this in more detail, the bath 26 broadly comprises an upper part 26A and lower part 26B. The widths of the upper part 26A and lower part 26B (horizontal width W shown in FIG. 2) are identical, and slightly larger than the width of the glass slides. As shown in FIG. 3, comparing the horizontal depths of the lower part 26B and upper part 26A, the horizontal depth of the upper part is larger. The horizontal depth variation (rate of variation) from the bottom to the top of the upper part 26A is also larger than the horizontal depth variation (rate of variation) of the lower part 26B, i.e. the upper part of the bath 26 is shaped like a horn. As the bath 26 has the above shape, it can be used for treatment by a small amount of reagent (first treatment mode) or a large amount of reagent (second treatment mode).

The horizontal depth D3 of the base of the lower part 26B is set to be slightly greater than the thickness of a glass slide, e.g. 1.2 mm. The horizontal depth D2 of the top of the lower part 26B is set to be a little greater than the horizontal depth D3 of the base, e.g. 2.0 mm. D2 is set to be larger than D3 to permit easy insertion of a glass slide from above.

When the horizontal depths D2, D3 are much larger than the thickness of a glass slide, the amount of reagent used in treatment by a small amount of reagent (first treatment mode) increases. D2, D3 should therefore be set near to the thickness of a glass slide, and should be of such an order as to permit easy insertion of a glass slide.

The height H2 of the lower part 26B is set to be of such an order as to be able to accommodate a major portion of a glass slide in the first treatment mode. Specifically, it should be set to a height such that a glass slide can be completely accommodated in the lower part 26B at least up to an area which is likely to be carrying a sample. For example, H2 may be set to 40 mm.

Figure 6:
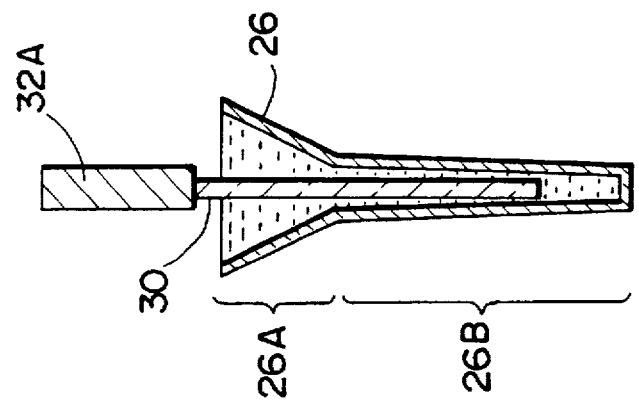
FIG. 6 is a diagram showing treatment by a small amount of reagent (first treatment mode).

The horizontal depth D1 of the top opening of the upper part 26A is of such an order that a holder 32A holding one end of a glass slide can be accommodated (FIG. 6). For example, D1 is 10 mm. In the first treatment mode, a glass slide supported by the holder 32A is inserted in the reagent bath 26, and the slide falls down until its lower end reaches the base of the lower part 26B.

A large amount of reagent can be held in the upper part 26A due to its large width. When a large amount of reagent is used (second treatment mode), treatment is performed by an amount of reagent equal to the sum of the large amount in the upper part 26A and the small amount in the lower part 26B, i.e. by a large amount of reagent.

The height H1 of the reagent bath 26 is set for example to 55 mm, the dimensions of its various parts corresponding to the size of a glass slide. The reagent amount used in the first treatment mode or the reagent amount used in the second treatment mode may be varied by adjusting the horizontal depth of the lower part 26B or the horizontal depth of the upper part 26A.

In the embodiment shown in FIG. 2, the cross-sectional areas of the upper part 26A and the lower part 26B are both set to progressively increase from the bottom to the top, however provided that the cross-sectional area varies in at least two steps, a single reagent bath 26 may be used for treatment by a large amount of reagent (second treatment mode) and treatment by a small amount of reagent (first treatment mode).

Two projecting flanges 42 are formed in an up/down direction on the inner wall of the lower part 26B of the reagent bath 26, as shown in FIG. 2. When a glass slide is inserted, it is inserted with the surface of the slide carrying the sample facing the inner wall on which the projections are formed. In other words, this flange 42 prevents contact with the inner wall of the lower part 26B and the sample, and also functions as a means of positioning the glass slide.

FIG. 4 is a partial section in the horizontal direction showing the glass slide inserted in the reagent bath 26.

When the slide 30 drops down, it is positioned by the two flanges 42 formed on the left and right edges of one of the inner walls 27 of the bath 26, and by the other inner wall 28 of the bath 26. A sample 44 on a sample adhesion surface 30A of the slide 30 is thereby separated from one of the inner walls 27 so that contact between the two is prevented. This ensures that reagent is supplied to the whole area of the sample 44, and prevents the sample 44 from falling off the slide 30 due to contact with the inner wall 27.

According to this embodiment, the flanges 42 are formed only on the lower part 26B, however flanges may also be formed on the upper wall 26A. The thickness of this flange 42 is set depending on the thickness of the sample 44. According to this embodiment, the thickness of the flange is set to approximately 100 µm when the thickness of the sample is approximately 30 µm. When the thickness of the sample is greater than this, the thickness of the flange 42 must be increased proportionately.

Next, the action of the physiological treatment apparatus shown in FIG. 1 will be described.

According to this embodiment, two treatment units 20, 22 having an identical construction are provided. While treatment by a reagent is being performed in one unit, preparation for treatment by the next reagent is being made in the other unit.

Specifically, while the glass slides 30 are inserted in the reagent baths 26 in one unit, reagent remaining from the immediately preceding treatment in the other unit is aspirated and removed by the plurality of aspirating nozzles 38. The next reagent is then introduced into a predetermined reagent bath 26 in the other unit, and the slides lifted out of one of the treatment units are inserted into the bath 26 in the other treatment unit where reagent treatment takes place.

By employing two units, performing reagent treatment in one of the units while preparation for treatment is carried out in the other unit, and then reversing the units, the efficiency of reagent treatment is greatly enhanced.

By providing the temperature controller 24 underneath the treatment units 20, 22, reagent treatment can be performed at a suitable temperature.

Figure 5:
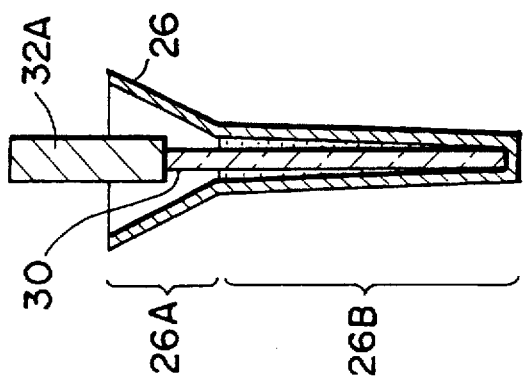
FIG. 5 is a diagram showing treatment by a large amount of reagent (second treatment mode).

FIG. 5 shows treatment by a large amount of reagent (second treatment mode). In this treatment, a predetermined amount of reagent is first introduced in the bath 26 by the pipette nozzle 14. It is preferred that the amount introduced is set so that reagent does not overflow outside the bath 26 when the slide 30 is positioned in the upper treatment position (second treatment mode) shown in FIG. 5.

A controller inside the body of the apparatus, not shown, controls introduction of reagent by the nozzle 14 and transport of the glass slides 30 by the holding mechanism 32. When treating with a large amount of reagent as shown in FIG. 5, the slide 30 does not drop completely to the base of the reagent bath 26, and is positioned in the aforesaid second treatment position. In this position, the sample on the slide 30 is treated by a large amount of reagent.

In the case of this treatment by a large amount of reagent, the slide 30 is given a periodic up/down motion with a fixed amplitude. The amount of reagent in contact with the sample on the slide 30 is thereby increased, and the reagent treatment is performed with high efficiency.

FIG. 6 shows treatment by a small amount of reagent (first treatment mode). In this treatment, a predetermined small amount of reagent is introduced in the reagent bath 26 by the nozzle 14. It is preferred that the amount introduced is set so that reagent wets all of the lower part 26B when the slide 30 has dropped to the base of the lower part 26B (first treatment position).

When the slide 30 is pulled down from above by the holding mechanism 32 so that it drops completely into the bath 26, the sample is wet by reagent which flows up between the inner wall of the bath 26 and the slide surface. In this case, contact between the sample and inner wall of the bath 26 is prevented by the flanges 42.

In the case of treatment by a small amount of reagent shown in FIG. 6, the slide 30 may be given an up/down motion with a fixed amplitude by moving the up/down stage 34 so as to move the holding mechanism 32 up and down.

According to this embodiment, the reagent amounts used for treatment by small and large amounts of reagent respectively, are set to an effective ratio of 1:4. For example, when it is possible to perform treatment using a small amount of a costly reagent, small amount treatment is selected. On the other hand, when it is necessary to perform treatment using a comparatively large amount of reagent, large amount treatment is selected. This selection is made by the controller depending on the reagent.

The reagent bath 26 in the aforesaid embodiment is formed so that both the lower part 26B and upper part 26A are wider from bottom to top. This has an advantage in that when the bath 26 is formed using a mold, it can be easily demolded.

The reagent bath 26 is formed of a material such as for example nylon which is stable to reagents such as xylene. Also to facilitate cleaning, etc., the reagent bath 26 may be of the disposable type so that the whole bath 26 can be replaced for each reagent treatment.

Treatment by a large quantity of reagent and treatment by a small quantity of reagent may be performed in the same way as described above on a pair of glass slides of which the surfaces not carrying sample are in contact. By inserting the pair of glass slides into the reagent bath, reagent treatment can then be performed on two samples using the same reagent. In this case, it is desirable to increase the horizontal depths D1, D2, D3 of the reagent bath by the thickness of one glass slide, and it is also desirable to provide the flanges 42 shown in FIG. 2 and FIG. 3 on both of the inner walls of the reagent bath 26 in order to protect the two samples.

What is claimed is:

1. An apparatus for treating a physiological tissue sample on at least one sample plate by a reagent, comprising:

at least one reagent bath having an upward opening through which said at least one sample plate is insertable vertically from above said opening, the cross-sectional surface area of an upper part of the at least one bath being larger than that of a lower part of the at least one bath, and a controller for controlling transport of said at least one sample plate and a supply of said reagent to said at least one bath, wherein:

in a first treatment mode, a first amount of reagent wherein a liquid surface level of said reagent is higher than a sample location on said sample plate during treatment is supplied to said at least one bath, and said at least one sample plate is inserted in said at least one bath up to a first treatment position, and in a second treatment mode, a second amount of reagent wherein said liquid surface level of said reagent is higher than the sample location during treatment is supplied to said at least one bath, and said at least one sample plate is inserted in said bath up to a second treatment position, said second amount being larger and the liquid surface level being higher than said first amount, and said second treatment position being higher vertically than said first treatment position.

2. A physiological tissue treatment apparatus as defined in claim 1, comprising a selector for selecting either said first treatment mode or said second treatment mode according to the type of reagent used.

3. A physiological tissue treatment apparatus as defined in claim 1, wherein a horizontal depth of said at least one reagent bath progressively increases from the lower part to the upper part.

4. A physiological tissue treatment apparatus as defined in claim 3, wherein the horizontal depth variation of the upper part of said at least one reagent bath is greater than the horizontal depth variation of the lower part of the said at least one reagent bath.

5. A physiological tissue treatment apparatus as defined in claim 1, wherein said opening which opens upwards is of such a size as to be able to accommodate a holder holding said sample plate.

6. A physiological tissue treatment apparatus as defined in claim 1, comprising a plate positioner for preventing a sample on said at least one sample plate from coming into contact with the inner walls of said at least one reagent bath.

7. A physiological tissue treatment apparatus as defined in claim 6, wherein said plate positioner comprises at least one flange formed on an inner wall of said at least one reagent bath.

8. A physiological tissue treatment apparatus as defined in claim 7, wherein said flange is formed in an up-down direction.

9. A physiological tissue treatment apparatus as defined in claim 1, wherein said controller periodically moves said at least one sample plate up and down while reagent treatment is performed.

10. An apparatus for treating a physiological tissue sample on at least one sample plate by a reagent, comprising:

- at least one reagent bath having an upward opening through which said at least one sample plate is insertable vertically from above said opening, said at least one bath further having a cross section larger toward a top end of said at least one bath and narrower toward a lower end of said at least one bath in which said at least one sample plate is introduced, and
- a controller for controlling the transport of said at least one sample plates, depth of insertion of said at least one plate and supply of said reagent, wherein:
- said controller determines a reagent amount introduced in said at least one reagent bath and an insertion depth of said at least one sample plate in said at least one reagent bath according to a selected treatment mode.

11. A physiological tissue treatment apparatus as defined in claim 10, wherein:

in a first treatment mode, said controller supplies a first reagent amount to said at least one reagent bath, and in a second treatment mode, said controller supplies a second reagent amount greater than said first reagent amount to said at least one reagent bath.

12. A physiological tissue treatment apparatus as defined in claim 10, wherein:

in a first treatment mode, said controller positions said at least one sample plate to a first treatment position in said at least one reagent bath, and in a second treatment mode, said controller positions said at least one sample plate to a second treatment position higher than the first treatment position in said at least one reagent bath.

13. An apparatus for treating a physiological tissue sample on a sample plate by a reagent, comprising:

- at least one reagent bath in which a pair of sample plates is introduced, and
- a controller for controlling the transport of said pair of sample plates and supply of said reagent, wherein:
- said controller determines a reagent amount introduced in said at least one reagent bath and by how much to insert said pair of sample plates in said at least one reagent bath according to a selected treatment mode.

* * * * *